United States Patent
Fuller et al.

(10) Patent No.: US 7,560,274 B1
(45) Date of Patent: Jul. 14, 2009

(54) CULTURE CHAMBER

(75) Inventors: Jess Paul Fuller, Hugglescote (GB); Tony Clayson, Ravenstone (GB); Robert MaClean Bird, Aston on Trent (GB); Timothy Burgess Clifford, Queniborough (GB); Anthony James Knights, Kittle (GB)

(73) Assignee: Cellon S.A. (LU)

( * ) Notice: Subject to any disclaimer, the term of this patent is extended or adjusted under 35 U.S.C. 154(b) by 0 days.

(21) Appl. No.: 09/979,915

(22) PCT Filed: May 30, 2000

(86) PCT No.: PCT/GB00/02073

§ 371 (c)(1),
(2), (4) Date: Apr. 1, 2002

(87) PCT Pub. No.: WO01/92462

PCT Pub. Date: Dec. 6, 2001

(30) Foreign Application Priority Data

May 28, 1999 (GB) .................................. 9912641.9

(51) Int. Cl.
C12M 1/12 (2006.01)
(52) U.S. Cl. .............. 435/297.1; 435/297.5; 435/299.2; 435/304.1; 435/304.2; 604/408; 604/410; 383/102
(58) Field of Classification Search ................. 435/180, 435/182, 395, 401, 402, 297.1–297.5, 299.1, 435/299.2, 304.1–305.4; 604/408, 410; 383/102
See application file for complete search history.

(56) References Cited

U.S. PATENT DOCUMENTS

| 3,997,396 | A | * | 12/1976 | Delente ...................... 435/400 |
| 4,649,114 | A | * | 3/1987 | Miltenburger et al. ....... 435/401 |
| 4,661,455 | A | * | 4/1987 | Hubbard ...................... 435/401 |
| 4,937,194 | A | | 6/1990 | Pattillo et al. |
| 4,939,151 | A | | 7/1990 | Bacehowski et al. |
| 5,686,304 | A | | 11/1997 | Codner |
| 5,702,945 | A | | 12/1997 | Nagels et al. |
| 5,786,215 | A | | 7/1998 | Brown et al. |
| 5,858,693 | A | * | 1/1999 | Cottingham .................... 435/8 |

FOREIGN PATENT DOCUMENTS

EP 461789 A1 * 12/1991

(Continued)

OTHER PUBLICATIONS

USPTO English translation of JP 57-156006 (Feb. 2005).*

(Continued)

*Primary Examiner*—William H Beisner
(74) *Attorney, Agent, or Firm*—Jones Day

(57) ABSTRACT

A culture chamber for use in a method of culturing microbiological material, which comprises a wall or at least a portion of a wall consisting of a gas-permeable membrane, a textured interior growth surface arranged for contact with the microbiological material being cultured and at least a portion of the external surface gas-permeable membrane being textured to enhance gas permeability. Preferably, the gas-permeable membrane is textured over the majority of both of its surfaces. This culture chamber provides enhanced gaseous exchange between the interior and exterior of the culture chamber and increased surface area within the culture chamber for cell attachment.

3 Claims, 10 Drawing Sheets

FOREIGN PATENT DOCUMENTS

| | | | |
|---|---|---|---|
| GB | 2268187 A | * | 1/1994 |
| JP | 54154473 A | * | 12/1979 |
| JP | 57156006 A | * | 9/1982 |
| JP | 08052816 A | * | 2/1996 |
| WO | WO 97/08291 | | 3/1997 |
| WO | WO 97/21347 | | 6/1997 |
| WO | WO 9721347 A1 | * | 6/1997 |
| WO | WO 99/55827 | | 11/1999 |
| WO | WO 0024437 A2 | * | 5/2000 |

OTHER PUBLICATIONS

Jensen. "Production of anchorage-dependent cells-Problems and their possible solutions." Biotechnology and Bioengineering, vol. XXIII (1981), pp. 2703-2716.*

Schmidt et al. "Macrophage response to microtextured silicone." Biometerials, vol. 13, No. 15 (1992), pp. 1059-1069.*

* cited by examiner

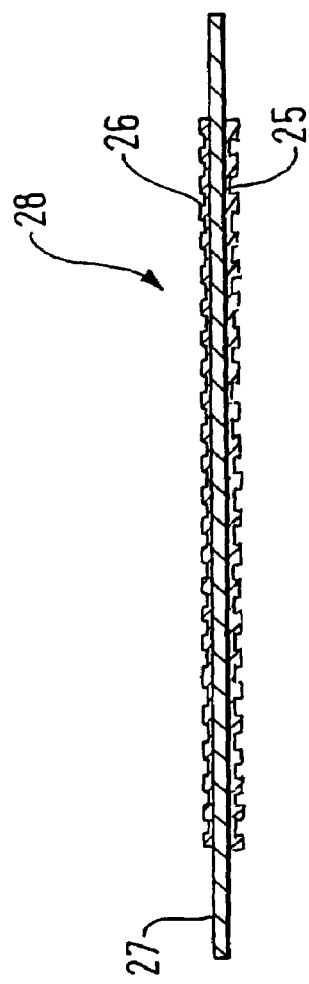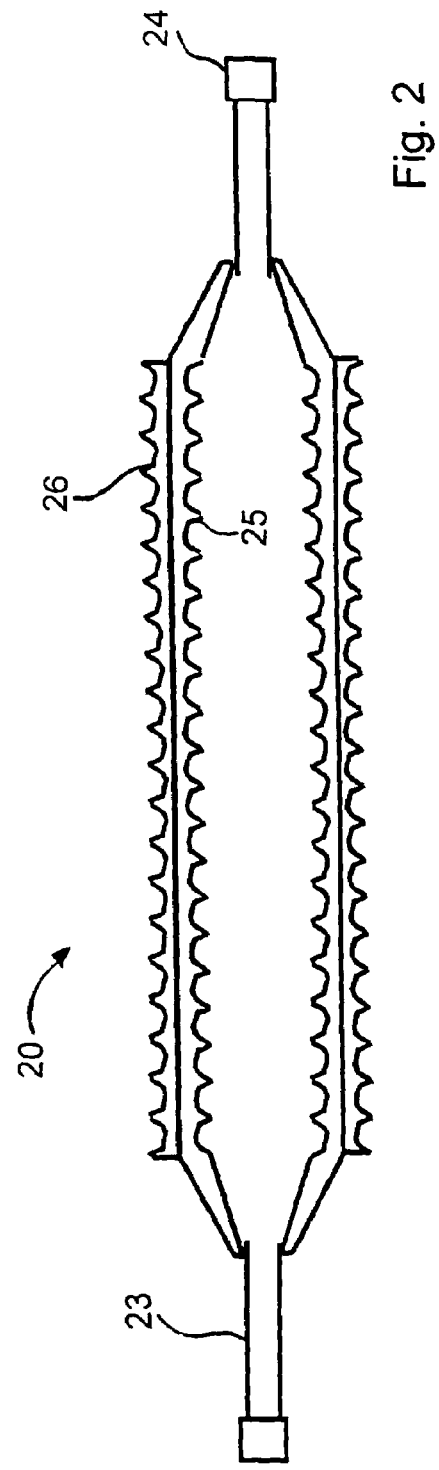

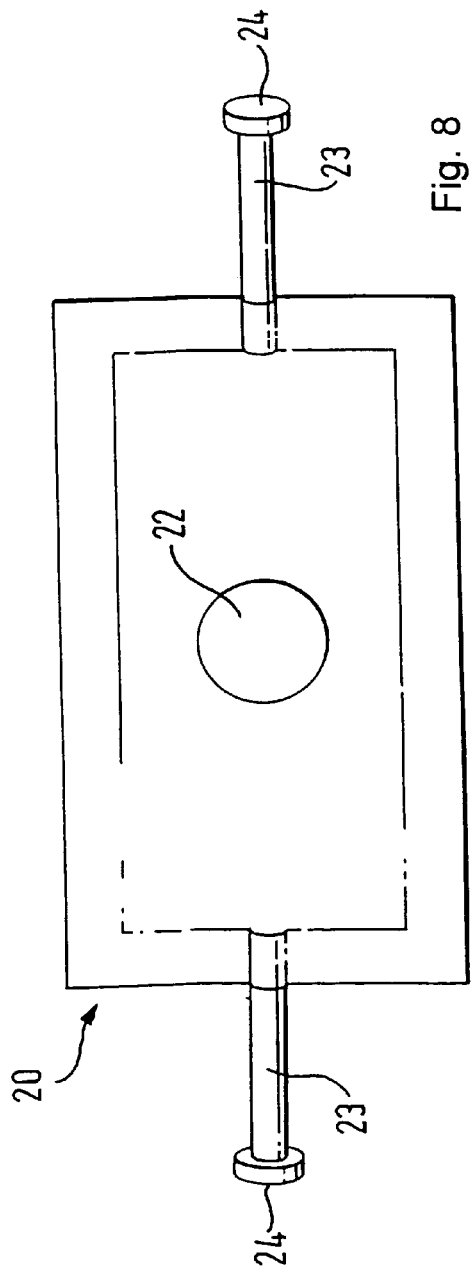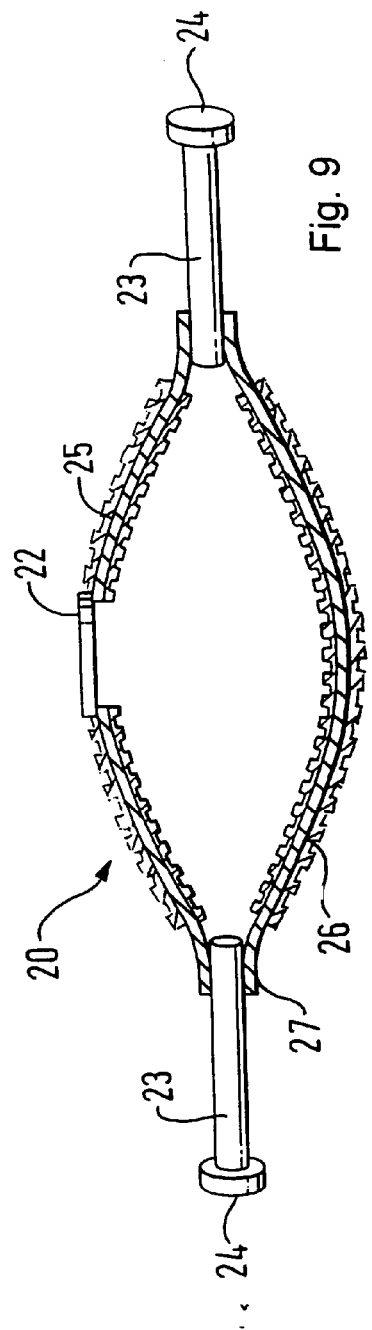

CULTURE CHAMBER

The present invention relates to culture chambers for use in a method of culturing microbiological material and, in particular, to culture chambers that provide increased gaseous exchange between the interior and exterior of the culture chamber and increased surface area for cell adhesion.

The general principles of culturing cells in vitro are well-established in the field of biotechnology, with the term "cell culture" being generally understood to refer to the growth and maintenance of cells, either as a cell suspension or an attached monolayer, usually devoid of structural organisation. "Tissue culture" has become the generic term encompassing culture of small fragments of animal, insect or plant tissue or whole embryonic organs, explanted to retain tissue architecture.

The cells in tissue and cell culture require oxygen and nutrients in order to grow and be maintained. There must also be provision for the removal of carbon dioxide and other metabolic waste products. The cells are generally provided with nutrients by way of the medium in which the culturing takes place. Different cells have different requirements and suitable nutrients may be included in the medium in order to meet the specific requirements of the type of cells being cultured. The culture chamber may be arranged to allow a throughput of nutrient medium, thereby providing a constant source of nutrients and removing waste products which are released into the medium by the cells. Providing the necessary gas exchange, that is the provision of oxygen and the removal of gaseous waste products such as $CO_2$, can be more problematic and often represents a serious limiting factor on cell and tissue culture. Many different ways of providing cells in culture with oxygen have been used, with varying degrees of success. One method is agitation of the culture chamber so that air is mixed in or the cells are exposed to the surface and therefore to oxygen. This method of oxygenation is most effective when the culture chamber contains as small a volume of medium compared to the chamber surface area as possible. Thus, the volume of nutrient medium one can use is severely limited when oxygen is supplied to the cells in this manner. An alternative method involves bubbling of oxygen-containing gases through the culture medium. However, whilst this method successfully provides the cells with oxygen, the bubbles can damage the relatively delicate cells.

The favoured method of providing cells in culture with oxygen is provided by diffusion into the culture chamber through a gas-permeable membrane. This diffusion overcomes the above mentioned problems associated with agitation and bubbling. The gas-permeable membrane may be in the form of tubes, or the like, passing through the culture chamber. Oxygen is then passed through said tubes and diffuses through the tube walls into the culture chamber. Alternatively, a wall or part of a wall of the culture chamber itself may be gas-permeable and thus allow oxygen to diffuse through said wall or wall portion and into the culture chamber. The amount of oxygen which is able to diffuse into the culture chamber is limited by the membrane surface area and gas-permeability. It should be noted that the membrane must be non-porous and must have some degree of structural strength, especially if it forms a wall or part of a wall of the culture chamber.

Despite the above described methods for providing gaseous exchange between the culture chamber interior and exterior, it has been found that the rate at which oxygen can be provided and gaseous waste products can be removed places a limit on the growth and proliferation of the cells. As the cells inside the culture chamber grow and proliferate, the oxygen requirement will increase and the waste products will build up, eventually preventing further growth and proliferation.

A further potential limiting factor encountered with known culture chambers is the surface area of the interior of the culture chamber available for cell adherence. There are two major types of cells grown in vitro, anchorage-dependent cells which require attachment to a growth substrate and anchorage-independent cells which can multiply in vitro without being attached to a surface. A smooth substrate, that is a smooth interior surface of the culture chamber provides a limited surface area for anchorage-dependent cells to attach and so will limit cell growth and proliferation. Furthermore, whilst many cells can attach to a smooth surface, certain "problem" cell types are unable to attach to a smooth surface.

A number of methods of increasing the surface area of the growth substrate in a culture chamber are known. These methods include elaborate structures which are placed within the culture chamber to provide additional cell attachment surfaces. The introduction of microcarriers into culture chambers is also know, the microcarriers comprising, for example, small glass spheres or sodium alginate.

It is an object of the present invention to provide a culture chamber which overcomes the above discussed limitations of the known culture chambers. According to a first aspect of the invention, a culture chamber for use in a method of culturing microbiological material is provided, the culture chamber having a wall or at least a portion of a wall consisting of a gas-permeable membrane, a textured interior growth surface arranged for contact with the microbiological material being cultured and at least a portion of the external surface gas-permeable membrane being textured to enhance gas permeability.

In a preferred embodiment, the textured interior growth surface is formed on the interior surface of the gas-permeable membrane. Preferably, the textured interior and exterior surfaces of the gas-permeable membrane overlap with one another, so that part of the gas-permeable membrane is textured on both of its surfaces. In an alternative embodiment, the textured portions on the interior and exterior of the gas-permeable membrane do not overlap. Herein, the term "overlap" means that the textured surfaces are substantially coincident on the opposite sides of the membrane.

A textured surface of the gas-permeable membrane increases the surface area through which gases may permeate. The permeability of the membrane itself will be limited by the area of both of its two surfaces. Thus, if one surface of the membrane is smooth and the other textured, the permeability of the membrane will be limited by the smaller surface area of the smooth surface. Thus, in order to benefit properly from the increased gas-permeability of the membrane afforded by a textured surface, both surfaces of the membrane must be textured. Ideally, at least 25% of the gas-permeable membrane is textured on both sides, more preferably, at least 50% is textured on both sides, and most preferably at least 90% of the gas-permeable membrane is textured on both its interior and exterior surfaces. This means that the degree of overlap of the textured surfaces is preferably at least 25%, more preferably 50%, and most preferably 90%. The textured surface on the culture chamber interior has the added advantage that it provides a greater area for cell attachment. Where both surfaces of the gas-permeable membrane are textured, the oxygen diffusing into the culture chamber is fed directly to the cells attached to the interior surface.

In a preferred embodiment, the gas-permeable wall and the textured surfaces are each formed from an organic polymer, optionally the same organic polymer. As the gas-permeable wall or portion of a wall of the culture chamber also provides the textured interior growth surface, cells may grow directly on a textured growth surface on the gas-permeable membrane, thus allowing high cell densities. The gas-permeable wall also has a textured exterior surface, thereby enhancing gas-permeability of the wall in particular in close proximity to the cells growing on the interior surface of the wall.

In a preferred embodiment, the gas-permeable membrane comprises silicone. Silicones surpass other elastomers in many performance categories because of their rigid silicon-oxygen chemical structure. The process of vulcanisation transforms this structure, allowing the silicon-oxygen polymer to become an elastic rubber. Silicone rubbers are stable throughout a temperature range of −46° C. to 232° C. They are odourless and tasteless. Silicone rubbers also do not stain or corrode with other materials. Advantageously, silicone rubbers are also not physically or chemically degraded or altered by contact with body fluids. Silicone rubbers can be formulated and tested for full bio-compatibility and compliance with guidelines for medical products. A further and particularly important advantage of silicone rubbers is that they have relatively high oxygen permeability within the scope of known polymers.

Preferably, at least one of the textured surfaces of the gas-permeable membrane is a layer of textured silicone. In a preferred embodiment of the invention, the textured silicone rubber layer is formed by a method comprising forming a coating of a silicone rubber precursor on a substrate, contacting a surface of the coating with a biologically-acceptable sacrificial filler, curing the resultant mixture and removing the sacrificial filler to form a layer of silicone rubber with a textured surface. In a preferred embodiment, the surface of the coating is contacted with the sacrificial filler under gravity, such that the sacrificial filler is substantially completely embedded in the coating. Alternatively, the sacrificial filler may be sprayed on to the surface of the coating, or may be applied loosely to the surface of the coating and then embedded by contacting the surface with a pressure roller. Preferably, the sacrificial filler is embedded to a depth of 0.1-1.0 mm, more preferably 0.1-0.5 mm, and most preferably 0.1-0.25 mm. In a preferred embodiment, a thicker layer of uncured silicone rubber is used. When the sacrificial filler is then sprinkled onto this thick layer, some particles will sink into the uncured silicone and other particles become positioned on top of them. When the rubber is cured and the sacrificial filler removed, these particles will create deep craters or channels which are particularly good for promoting cell adhesion. This thicker textured silicone layer may be applied to either surface of the gas-permeable membrane, or to both. Preferably, the thicker layer of textured silicone is twice as thick as a normal silicone layer. In an alternative embodiment, the sacrificial filler is scattered or sprinkled over the surface of the coating, such that the sacrificial filler is only partially embedded in the surface. The latter technique can be used to provide the surface of the silicone rubber with a less uniform texture that is particularly suitable for growing certain types of adherent cells. Preferably, the resultant textured surface is micro-cupulated, i.e., cratered or pitted, the micro-cupules having a depth of less than 1 mm, preferably a depth of 0.5-0.1 mm. In a preferred embodiment, the micro-cupules measure less than 2 mm across, preferably less than 1 mm across, and, most preferably, less than 0.5 mm across. Silicone rubbers are available with a wide range of different physical properties, both in the uncured and cured state, and their methods of cure also differ widely. Consequently, the nature and properties of the silicone rubber used can affect the manufacturing process and the choice of a suitable silicone rubber precursor can be important. The silicone rubber precursor should be selected with due consideration to the manner in which the mixture is to be applied to the substrate, the conditions required for curing, and the desired properties of the end product. The uncured silicone rubber should usually have an appropriate viscosity for the method of its application to the substrate, and should retain its general form once the sacrificial filler has adhered to its surface. The conditions for curing must generally be compatible with both the substrate to which the uncured silicone rubber is applied and the sacrificial filler that adheres to the surface. Finally, the quality of the silicone rubber used should be selected in light of the intended application of the final product. In an especially preferred embodiment, silicone rubber paint RTV 118 (General Electric Co., Connecticut, USA) or R2-113 (NuSil Technology, California, USA) are used. Silicone rubber precursors which are widely available commercially may be used, for example, from Dow Chemical Corporation, Midland, Minn., USA, or from GE Silicones Europe, Bergen op Zoom, the Netherlands. In a preferred embodiment, the silicone rubber precursor is one that can be cured or vulcanised at room temperature. This obviates the need to expose the mixture to elevated temperatures, which is particularly useful as some sacrificial fillers become unstable and decompose at elevated temperatures, thus making it difficult to control the final form of the structured silicone rubber. In order to assist adhesion of the silicone rubber layer to certain materials, it may be necessary to apply a conventional adhesive, such as a mineral spirit-based primer, prior to deposition of the silicone layer. In a preferred embodiment, the primer used is silicone rubber primer SS 4155 (General Electric Co., Connecticut, USA).

Preferably, the biologically acceptable sacrificial filler used in the method of producing the textured layer is biocompatible, such that it is innately non-toxic and does not leave a toxic residue. This is of particular importance where the structured silicone rubber is intended for use in tissue culture and medical applications, although a number of further factors also need to be considered when choosing a suitable sacrificial filler. For example, the sacrificial filler should preferably not react with the silicone rubber, either in its precursor form or in its cured state. The filler should also preferably be soluble in order to facilitate its removal by dissolution and the solvent used to dissolve the material should preferably not react with the silicone rubber. If the silicone rubber is to be cured at elevated temperatures, it is usually desirable to use a sacrificial filler that is stable at the curing temperatures, since materials that melt or decompose at high temperatures may be unsuitable, particularly if a structured silicone rubber having a high degree of regularity is desired. Finally, for commercial reasons, it is generally desirable that the sacrificial filler should be relatively inexpensive and readily available. In a preferred embodiment, the sacrificial filler is ground, prior to contacting the silicone rubber precursor. This has the advantage of allowing the resultant structure of the silicone rubber to be controlled much more accurately. Any suitable method for grinding the sacrificial filler may be used, although it has been found that wet-milling the sacrificial filler, prior to mixing with the silicone rubber precursor, gives good results. However, the sacrificial filler may also be ground by dry milling, preferably under an inert or dry atmosphere, such as under dry nitrogen or argon gas. In a preferred embodiment, the sacrificial filler is milled to a particle size of 0.005-1 mm, preferably 0.01-0.5 mm, and most preferably 0.05-0.1 mm. These particle sizes produce micro-cupels of the same size in the resultant textured silicone layer. In a further embodiment, the sacrificial filler is granular and, preferably, crystalline, although certain amorphous fillers may also be suitable. Inorganic salts have been found to give particularly good results, although certain crystalline organic compounds, such as simple saccharides, may often be equally effective. Where the sacrificial filler is an inorganic salt, it is especially preferred to grind it first by milling it in an organic solvent, since this gives good control over resultant particle size. Preferably, the sacrificial filler is an inorganic salt selected from the group consisting of metal halides, metal carbonates and metal bicarbonates, especially one selected from the group consisting of lithium bicarbonate, sodium bicarbonate, potassium bicarbonate, lithium chloride, sodium chloride and potassium chloride. In an especially preferred embodiment, the sacrificial filler is sodium bicarbonate or sodium chloride, preferably of high purity, such as US Pharmacopoeia grade sodium bicarbonate or sodium chloride. In this last embodiment, the sodium bicarbonate or sodium chloride is preferably wet-milled under xylene, although other volatile organic solvents may also be used. In a further embodiment, the ground sacrificial filler is classified, prior to contacting the silicone rubber precursor to ensure uniform particle size distribution, for example, by passing the ground material through sieves or by using a Malvern® Particle Sizer. In another embodiment, the sacrificial filler is removed by dissolution, preferably in an aqueous solvent. In the latter case, the sacrificial filler is desirably chosen so that it does not cause swelling of the silicone rubber when removed with an aqueous solvent.

In one preferred embodiment of the present invention, the micro-cupels on the interior surface of the culture chamber are larger than those on the exterior surface. The larger micro-cupels help to promote cell adhesion inside the culture chamber.

There are several ways in which cell adhesion to the textured silicone layer may be enhanced. In one embodiment, at least a portion of the free groups that are normally present in the silicone rubber are chemically modified, for example using potassium hydroxide or sodium hydroxide, thereby converting them into —OH groups. These —OH groups are then chemically converted to form positively charged groups, for example, by reaction with diethylaminoethylbromide to give DEAE moieties, or to form negatively charged groups, for example, by reaction with iodoacetic acid, to give carboxylate moieties. Such chemical modification of groups serves to enhance or promote cell adherence. In an alternative embodiment, the surface of the silicone rubber may be charged electrostatically, for example, by bombardment with electrons. Alternatively, the surface characteristics of the silicone rubber may be modified by applying a thin coating of a suitable polymer, so as to make it more adherent to certain cells, whilst still retaining a sufficient degree of gas permeability. Any suitable bio-active polymer may be used, such as one selected from the group consisting of proteins, lipoproteins, lipopolysaccharides and polysaccharides. In a preferred embodiment, the silicone rubber precursor also includes at least one additive that is not removed with the sacrificial filler and serves to impart desired physical properties on the resultant silicone rubber. For example, the additive may be a metal powder or carbon black, which can be used to render the silicone rubber electrically conductive. Alternatively, the additive may be stainless steel powder or iron oxide, which can be used to increase the density of the silicone rubber. The additive may also be an inert substance, such as glass, which can be used to render the silicone rubber mechanically rigid. However, many other suitable additives will also be apparent to those skilled in the art.

Preferably, the culture chamber has at least one port extending between the interior and the exterior of the chamber. More often, however, there will be at least two ports, preferably including an inlet and an outlet port. In addition, one or more septum ports may also be provided, to reduce the risk of contamination when introducing various substances to the culture chamber. In an embodiment, at least one of the inlet and outlet ports are septum ports.

In a further embodiment of the invention, the surface area available for cell adhesion is further increased inside the culture chamber by including one or more additional cell attachment means. In one embodiment, the additional cell attachment means is one or more gas-permeable sheets, which are made in the same way as the textured gas-permeable sheets described above. Preferably, these sheets are also textured on both of their surfaces, thereby providing a large surface area. In an alternative embodiment, the additional cell attachment means is a textured semi-permeable sheet. In yet another embodiment, the additional cell attachment means is a porous structure, the pores providing a surface to which the cells become anchored within the culture chamber. In a preferred embodiment, the porous additional cell attachment means is porous silicone rubber. The porous additional cell adhesion means may be in the form of sheets or pellets.

Preferably, the porous silicone is made by mixing a sacrificial filler into uncured silicone rubber, so that it becomes dispersed throughout the rubber. Next, the rubber is cured and finally the sacrificial filler is removed, leaving a system of pores and channels throughout the silicone rubber structure. The pores of the silicone rubber provide sites of attachment for cells or tissues, so that the cells or tissues may be substantially trapped within the resultant structure. The resultant mixture may be shaped prior to curing, preferably by moulding or extrusion. In a preferred embodiment, the average size of the pores formed is 1 µm-0.5 mm, preferably 10 µm to 0.2 mm, and most preferably 50 to 150 µm in diameter. Preferably, the porous silicone rubber is cut to a desired size or shape once cured. The inventors of the present invention have found that the use of certain sacrificial fillers can have an adverse effect on the resultant silicone rubber. For example, the use of sodium chloride can cause the silicone rubber to swell, depending upon the conditions. In order to avoid, this, it is desirable to use a sacrificial filler that does not cause swelling or adversely effect the resultant silicone rubber. Sodium bicarbonate has been found to be particularly effective in satisfying such criteria, although a number of other sacrificial fillers may be equally effective. If sodium bicarbonate is to be used as a sacrificial filler, it decomposes and, therefore, "blows" the material at temperatures above approximately 180° C. Consequently, it is necessary to adapt the manufacturing process so as to avoid temperatures above 180° C., for example, by selecting silicone rubbers, which cure at lower temperatures. Many of the alternative sacrificial fillers are toxic, leave toxic residues when dissolved, or are problematic at moderate temperatures required for working with silicone rubber. The additional cell attachment means may be either held in place within the culture chamber, or it may be "free-floating". Where the additional cell attachment means is a sheet, it may be used to divide the culture chamber into two or more compartments. Where the additional cell attachment means comprises a semi-permeable membrane, the contents of the two or more chambers will remain separate. The compartments within the culture chamber may either share inlet/outlet ports or have separate ones so that the contents of the compartments can be controlled independently of one another. The use of such additional cell attachment means is only worthwhile where the culture chamber provides sufficient gaseous exchange between the chamber interior and exterior to supply the increased number of cells with enough oxygen, whilst also removing the gaseous waste products.

In a second aspect of the invention, the culture chamber according to the first aspect of the present invention is in the form of a flexible bag or envelope. In recent years, flexible culture bags have become increasingly popular, offering a number of advantages over traditional cell culture apparatus, such as multi-well plates, flasks, roller bottles and spinner flasks. For example, culture bags represent closed systems, thus reducing the risk of contamination, as well as taking up less storage and incubator space. In addition such culture bags can often be produced relatively inexpensively, making them effectively disposable and reducing any need to sterilise them for re-use. Silicone rubbers have a relatively high oxygen permeability compared to most known polymers, and tubing or membranes made from such materials are well-suited for use in cell culture, where they are able to provide improved diffusion of oxygen to the cells. Silicone rubbers not only provides gas permeability (including oxygen and carbon dioxide) but also vapour transmission, structural integrity, resilience and temperature resistance, all of which are desirable in cell and tissue culture. International patent application no. PCT/US96/20050 (Avecor Cardiovascular, Inc.) discloses a cell culture bag formed from a plurality of thin, spaced, gas-permeable silicone membranes, whose gas exchange rate is claimed to be significantly higher than most conventional culture bags. However, although such bags may be capable of sustaining higher cell densities and cell viability, they are ultimately limited by the surface area of the bag. Moreover, the interior surfaces of such bags are smooth and, thus, provide poor cell attachment features, making them unsuitable for efficient cell culture of anchorage-dependent cells. Furthermore, certain "problem" cell types are unable to attach to the smooth interior surface of the bags. An elaborate (and seemingly expensive) method of increasing the surface area available for cell adhesion is described in U.S. Pat. No. 4,937,194 (Baxter International, Inc.), which discloses a flexible bag containing an internal cellular structure, such as a honeycomb type structure with hexagonal channels passing through it, serving as adherent sites for cells being cultured. This document also proposes the use of microcarriers, such as small glass spheres or sodium alginate, to increase the surface area available for cell adherence inside the bag. There is a need, therefore, to overcome some of the aforementioned disadvantages.

The culture bag of the present invention provides an increased growth substrate surface area for cell attachment, as well as providing increased gaseous exchange between the bag interior and exterior. Moreover, the bag structure is simple and inexpensive to manufacture. In a preferred embodiment, the bag is made from at least one textured gas permeable membrane as described above and preferably all of the walls making up the bag comprise such membranes. As already described above in relation to the culture chamber, the culture bag preferably also includes one or more ports, extending between the bag interior and bag exterior. Such ports may be used for introducing nutrient medium, taking samples, adding further ingredients, etc. The ports should preferably have valves, locks or the like, to avoid contamination of the bag interior. In a preferred embodiment, the culture bag is provided with an inlet and an outlet port with luer locks, and a septum port for taking samples or introducing substances into the bag. The ports are desirably positioned between the sealed edges of the culture bag. It has been found that the application of a textured surface to a culture bag wall in accordance with the invention can result in the wall becoming opaque. In a preferred embodiment, therefore, the culture bag also includes at least one portion of membrane to which no textured surface layer has been applied, this area serving to act as a transparent window, thus allowing a user to see inside the culture chamber. In a further embodiment, the culture chamber also includes a valve means, allowing the release of gases that build up during cell growth and may form an air bubble inside the bag. The presence of a bubble within the chamber can prevent colonisation on the surface area adjacent the bubble because the surface will not be in contact with the culture medium. Thus, the presence of a valve in the culture chamber wall helps to minimise the size of any gas bubbles, thereby allowing a larger surface area of the bag to remain in contact with the nutrient medium and to be available for cell attachment. Almost complete colonisation on the interior chamber surface is, therefore, possible, increasing the efficiency of the culture chamber. Desirably, the valve comprises a filter means, allowing gasses to diffuse out of the chamber but preventing microbial contamination. In a preferred embodiment, the valve means comprises one or more layers of a hydrophobic material, such as a hydrophobic PTFE membrane, preferably having a thickness of around 0.25 mm and a porosity of 0.2 microns. However, other suitable forms of valve means will also be apparent to those skilled in the art. In a preferred embodiment, the culture bag further comprises a second chamber separated from the first chamber by means of a semi-permeable membrane. The second chamber preferably has an access means separate from that of the first chamber.

In a third aspect of the invention, there is provided an apparatus comprising a plurality of culture chambers according to the invention in its first aspect, for use in a method of culturing microbiological material. In an embodiment, the inlets of the culture chambers are interconnected and the outlets of the culture chambers are interconnected. In a preferred embodiment, the apparatus has at least one further chamber(s) having a semi-permeable wall that is positioned within each culture chamber, each semi-permeable chamber (s) having an inlet that is interconnected with the inlet of any other semi-permeable chambers and having an outlet that is interconnected with the outlet of any other semi-permeable chambers. In a preferred embodiment, the apparatus is filled with liquid medium, which has first been inoculated with a desired cell line. The assembly of reactor tubes may then be arranged to be rotated or agitated, for example, using machinery such as that employed for conventional roller bottles. Rotation may be continued until cell confluence is obtained, as evidenced by the levelling of the rate of glucose uptake. The inner surfaces of the reactor tubes are, therefore, extensively coated with the cells as this stage. If appropriate, rotation may be interrupted for replacement of the medium in the reactor. The reactor tubes can then be removed from the rollers and connected to a suitable media reservoir. A continuous stream of liquid nutrient medium may be arranged to pass through the reactor envelopes, the product being harvested at the outlet. During this procedure, it is desirable to provide airflow over the reactor, to assist oxygenation. The productivity and efficiency of the growth process, especially in the case of anchorage dependent cells, can be substantially enhanced using the bio-reactors according to the invention, especially when compared with conventional reaction vessels that do not utilise oxygen permeable containers and, thus, cannot sustain cell growth process in the manner permitted by the invention.

In another embodiment, the culture chambers further include semi-permeable chambers positioned within them, such as, for example, semi-permeable chambers made of cellulose acetate. The semi-permeable chambers are arranged to be separately connected to common inlets and outlets at their respective ends. In this embodiment, the bio-processing operation involves the following procedures. First, the cells grown to perform the bio-processing function are attached to the textured surface of the culture chamber using the method described above. The culture medium is then removed from said culture chambers. Next, the nutrient medium is passed through the culture chambers textured interior surface, which are now coated with cells. The media is introduced from a reservoir through the inlet at one end of the culture chambers, issuing at the outlet on the opposing end. If desired, the medium may be recycled from the outlet, to return again to the inlet of the chambers. The liquor to be processed, such as blood, for example, is then arranged to flow through the semi-permeable chambers. The liquor is introduced for this purpose at the inlet of the semi-permeable chambers, and issuing at the outlet on the opposing end. The liquor is preferably passed through the semi-permeable chambers in opposing direction to that of the nutrient medium. During this procedure, nutrients from the medium feed the cells adhering to the coating of the culture chambers. At the same time, waste materials in the process liquor, such as ammonia, pass across the semi-permeable membrane and are processed to harmless compounds by the cells in the culture chamber. In addition, advantageous products produced by the cells in the culture chamber pass back across the membrane into the process liquor. The treated liquor is finally collected at the outlet of the culture chambers. In a preferred embodiment, the apparatus is especially adapted for bio-processing of liquors containing particulate matter, such as blood cells or cell debris. The continuous flow system according to the invention is especially applicable to the processing of whole blood, for example, in an artificial extra corporeal organ substituting or supporting the functions of the human liver. Advantageously, the system obviates the need of separating the particulate matter prior to processing and then having to reunite the constituents. It is also envisaged that the culture chambers and apparatus according to the invention may have other medical applications, such as for expansion of other primary cell types, or for use as an ex vivo model for drug metabolism if colonised with hepatocytes and the like. In a yet further embodiment, the culture chamber is closed and there is a flow of media through the semi-permeable membrane that feeds the cells within the culture chamber. This means that both the cells and the cell products will become concentrated within the culture chamber, as neither is able to pass out through the membrane. This concentrated solution of cells and/or product can then be harvested periodically through ports which communicate with the interior of the culture chamber.

In a fourth aspect of the invention, the culture chamber according to the first aspect of the invention is a well for use in a method of culturing microbiological material. In a preferred embodiment, the textured gas-permeable portion of the wall is positioned at or near to the base of the well.

In a fifth aspect of the invention, there is provided a microtitre plate having at least one well according to the invention in its fourth aspect. The wells help to increase both the quantity of cells that can be grown in a microtitre well of a given size, as well as their metabolic activity. As microtitre wells become increasingly minimised in size, the number of cells that can be grown in each well, for example, for drug metabolism studies, is also reduced because of the decrease in available growth surface area. Moreover, those cells that can be grown are also starved of oxygen due to the decrease in gassing surface to volume ratio. The microtitre plate according to the invention helps to alleviate these problems by firstly increasing the gaseous exchange between the interior and exterior of the well and by increasing the available surface area for cell attachment.

In order that the invention may be better understood, examples of the various aspects will now be described, by way of illustration only and with reference to the accompanying drawings, wherein:

FIG. 1 is a cross-sectional view of a membrane wall of the culture chamber in accordance with the present invention;

FIG. 2 is a schematic cross-sectional view of a simple culture chamber in accordance with the invention;

FIG. 8 is a schematic plan view of a culture bag in accordance with the second aspect of the invention;

FIG. 9 is a schematic cross-sectional view of the culture bag of FIG. 8;

Figure 3:
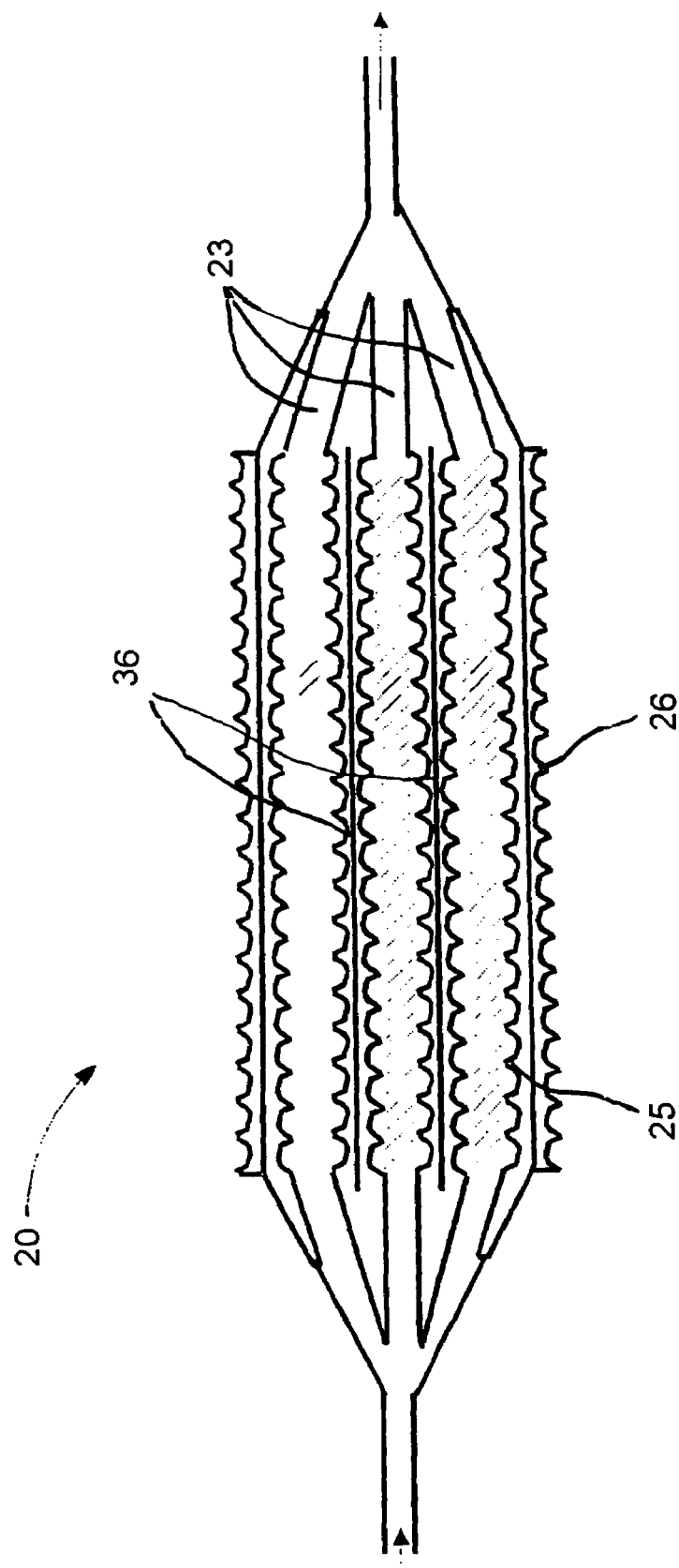
FIG. 3 is a schematic cross-sectional view of a culture chamber with additional textured membranes positioned within the chamber.

FIG. 1 shows a textured membrane 28 which will form part of the wall of the culture chamber according to the first aspect of the present invention. The structure comprises a gas-permeable membrane 27, and textured surfaces 25 and 26. Each bag membrane 28 is prepared by covering the edges 27 of a smooth silicone rubber sheet with a mask and applying a layer of room-temperature vulcanising liquid silicone rubber to the exposed central portion of the sheet. Next, vacuum-dried salt is sprinkled over the layer of liquid silicone rubber so that it is uniformly covered. The liquid silicone rubber is then cured and the salt is washed out, producing a membrane 28 with a cratered or micro-cupulated surface 26. This process is carried out to produce textured layers on both surfaces of the gas-permeable membrane.

FIG. 2 shows the membrane of FIG. 1 incorporated into a culture chamber. The chamber comprises two textured gas-permeable membranes which are welded together along their outer edges to form a culture bag. Inlet and outlet ports 23 extend between the inside and the outside of the bag, each port 23 being provided with a lock or valve 24. Nutrient medium may be introduced into the chamber and removed from the chamber via these ports. The culture chamber may be provided with a continuous flow of nutrient medium, or it may be filled with medium and then sealed using the valves or locks for simple batch processing.

FIG. 3 shows a multi-layer perfusion system. The culture chamber includes a number of additional membranes. The additional sheets 36 are textured on both surfaces. They may be sealed to one another around their edges, thereby creating separate compartments. These compartments may then be provided with medium by individual inlet/outlet ports. Alternatively, the additional sheets 36 may not be sealed along at least one edge, so that the nutrient medium can move around the chamber and the between the additional sheets.

Figure 4:
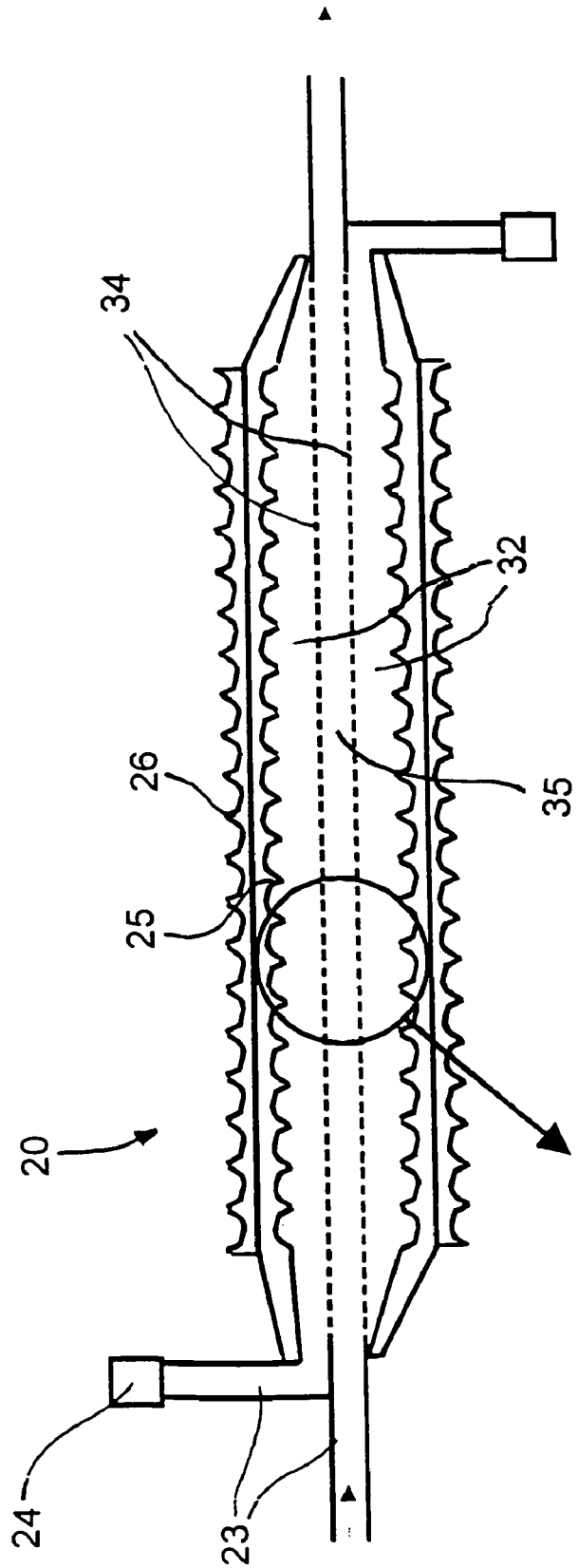
FIG. 4 is a schematic cross-sectional view of a culture chamber used for concentrating the cells and their products.
Figure 5:
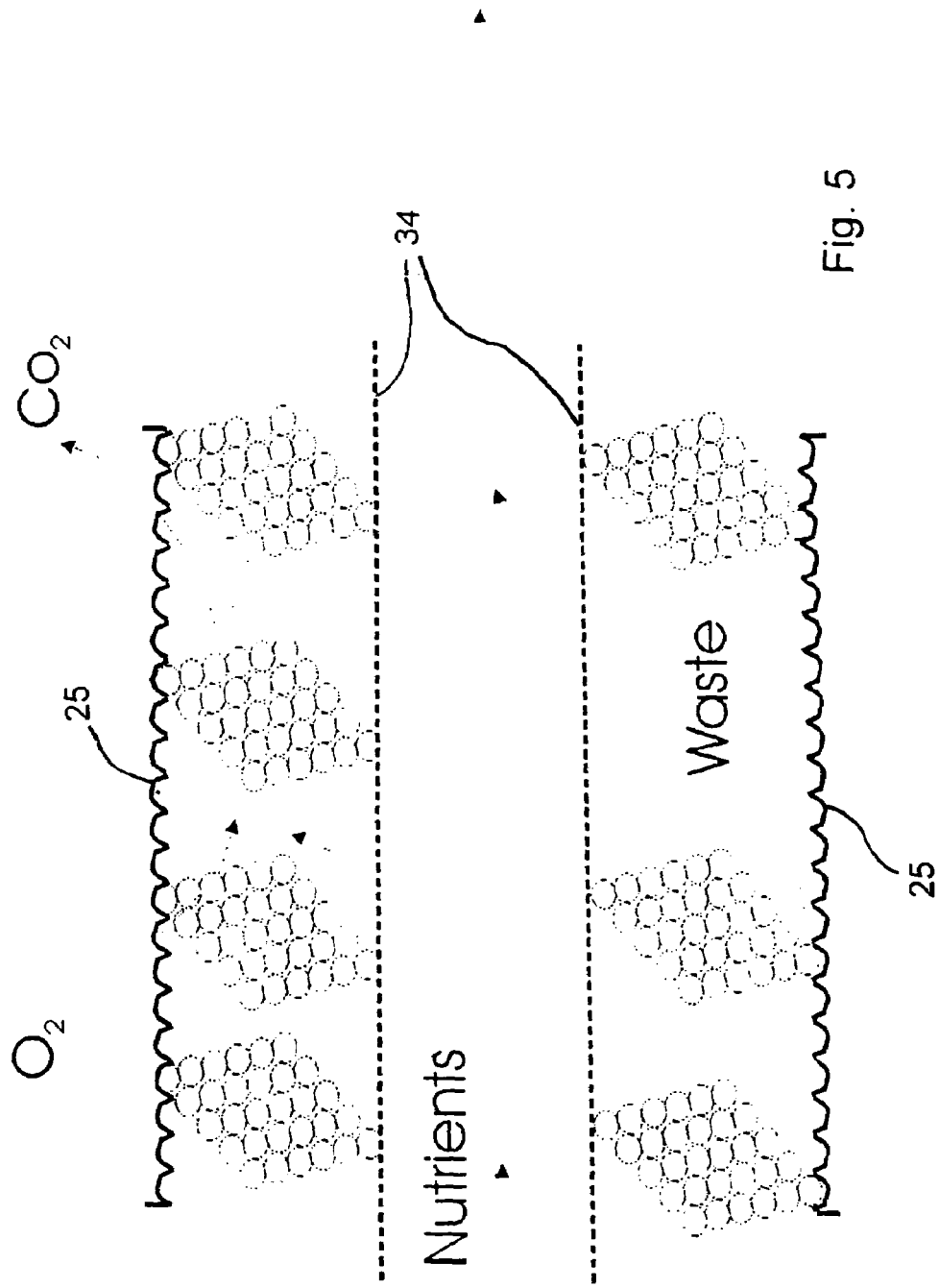
FIG. 5 is a schematic diagram of the movement of nutrients and waste, etc. within the culture chamber shown in FIG. 4.

FIG. 4 shows a culture chamber wherein the chamber is divided into three compartments by semi-permeable membranes 34 positioned inside the culture chamber. This culture chamber is used as a cell/cell product concentration device. The innermost compartment 35 is provided with a continual throughput of nutrient medium. The other, outermost compartments 32 contain cells. As shown in FIG. 5, the nutrients from the medium diffuse through the semi-permeable membranes 34 into the outermost compartments. Oxygen diffuses into the outermost compartments 32 through the external culture chamber wall. Waste products diffuse out of the compartments containing the cells through the semi-permeable membrane 34 and flows out of the culture chamber. Carbon dioxide produced by the cells diffuses out through the external culture chamber membrane. The cells or their products may be harvested from the otherwise closed compartments 32 through the ports 23 with valves or locks 24.

Figure 6:
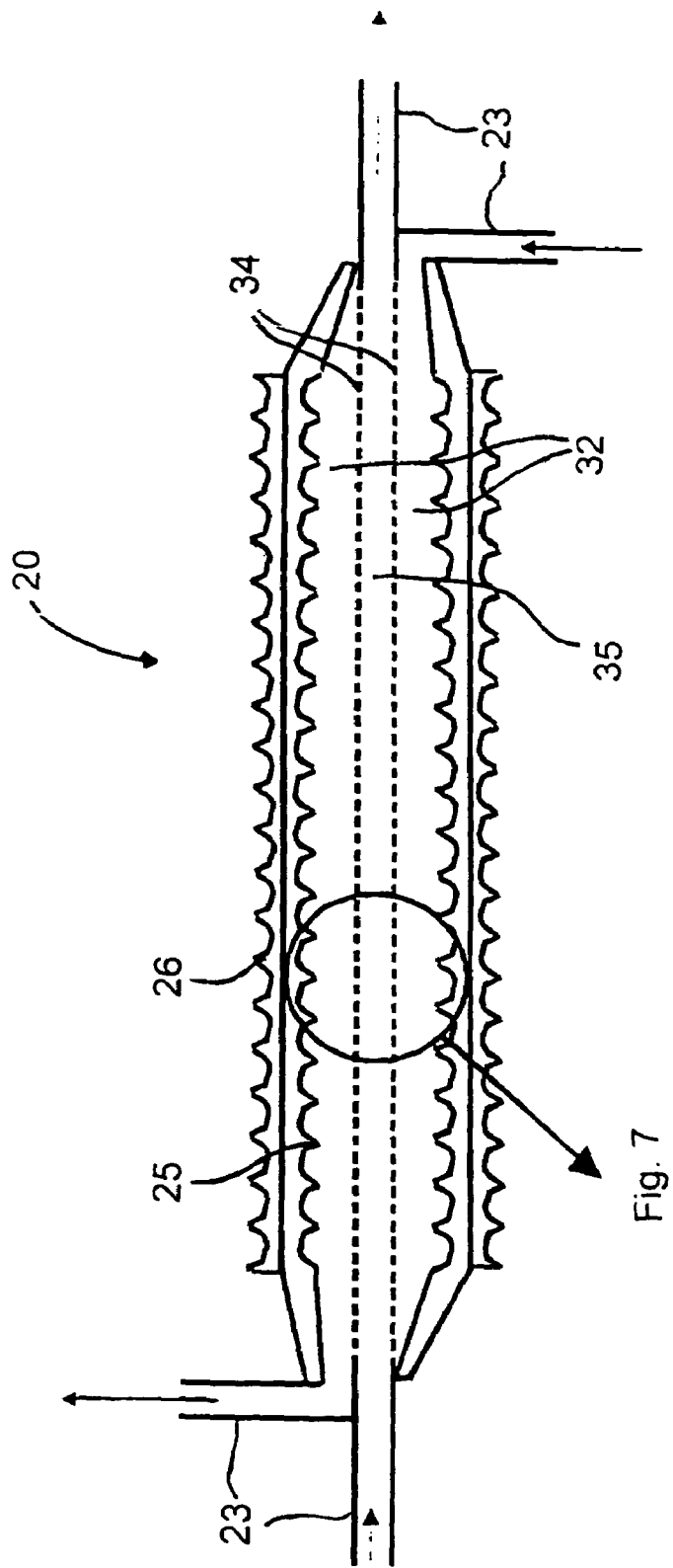
FIG. 6 is a schematic cross-sectional view of a culture chamber used as a bio-reactor.
Figure 7:
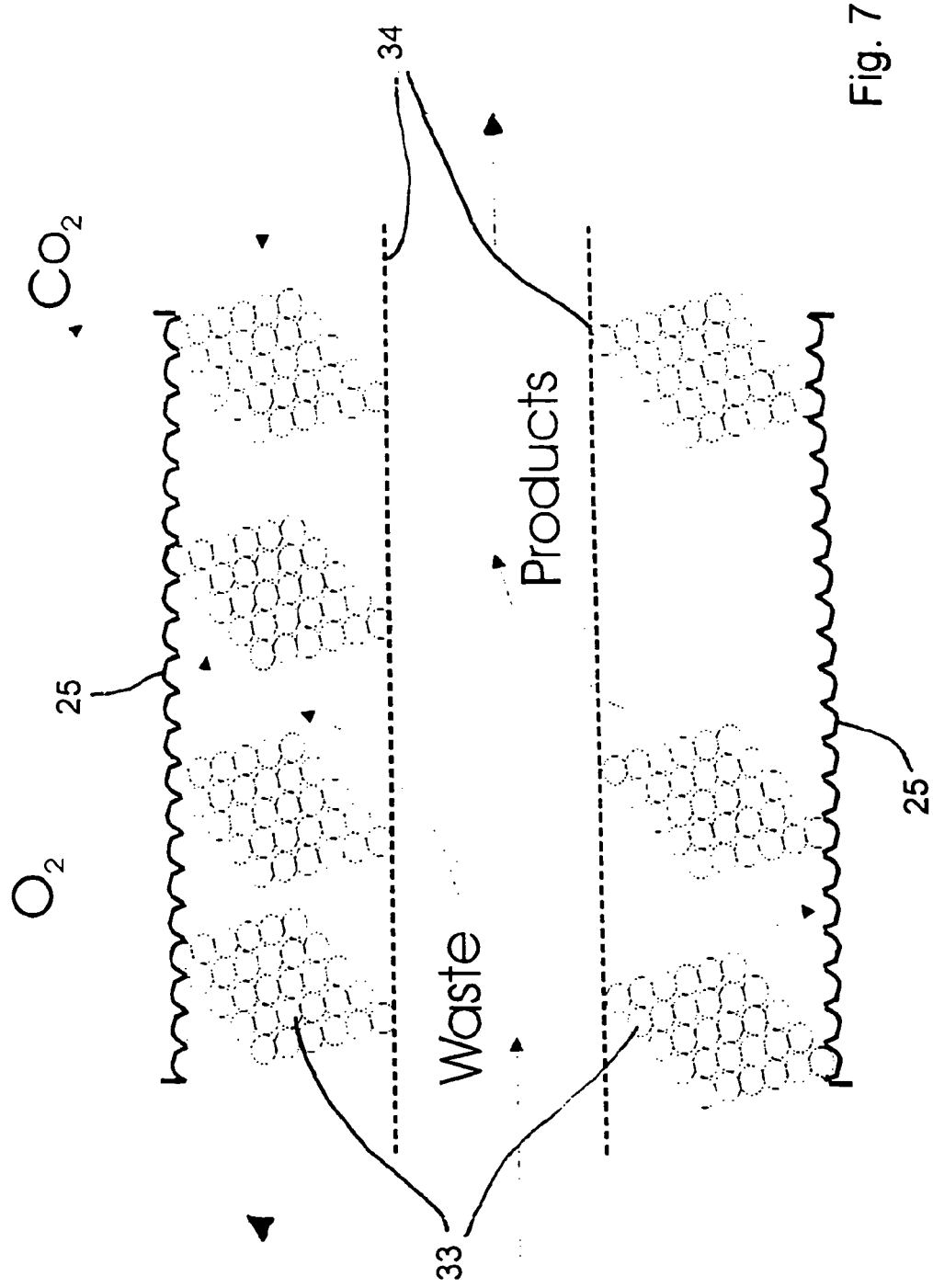
FIG. 7 is a schematic diagram of the movement of nutrients and waste, etc. within the culture chamber shown in FIG. 6.

FIG. 6 shows a culture chamber wherein the chamber is divided into three compartments by semi-permeable membranes 34 positioned inside the culture chamber. This culture chamber is used as a bio-reactor. The innermost compartment 35 is provided with a continual throughput of liquor which is to be processed. The other, outermost compartments 32 contain bio-processing cells, such as hepatocytes, and are provided with a throughput of fresh nutrient medium. As shown in FIG. 7, the nutrients required by the cells are provided by the nutrient medium and waste products are "washed away" as the medium passes through the compartment. Oxygen diffuses into the outermost compartments 32 through the external culture chamber wall and carbon dioxide produced by the cells diffuses out through the external culture chamber membrane. The cells in the outermost compartments process waste products from the liquor in the innermost compartment 36 which diffuse through the semi-permeable membrane 34. The products of the bio-processing cells diffuse into the innermost compartment, so that processed liquor is removed from the culture chamber.

Figure 10:
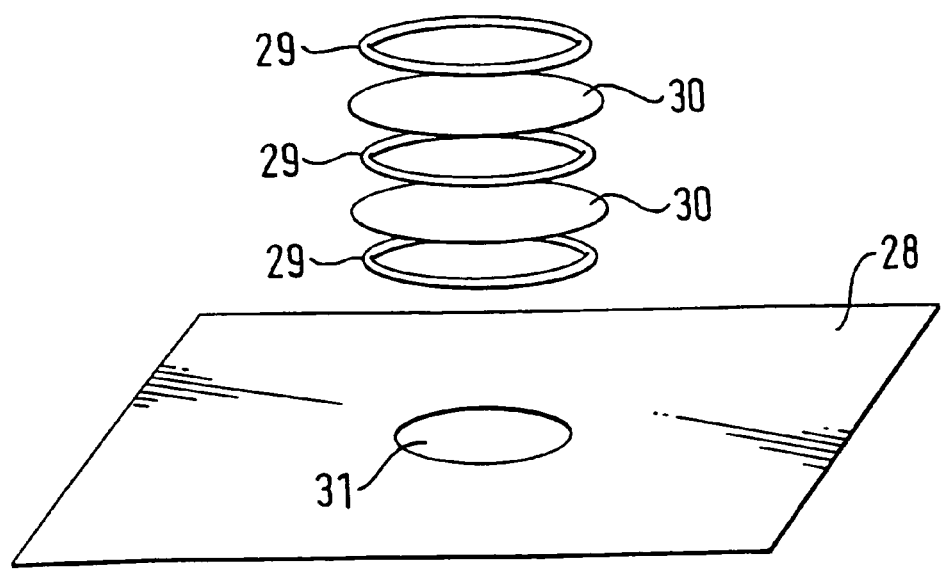
FIG. 10 is an exploded view of the valve of the culture bag of FIGS. 8 and 9.

In FIGS. 8 and 9, a culture bag 20 comprises two membranes 28 joined at their outer edges 27, each membrane 28 having textured interior and exterior surfaces 26. A degassing valve 22 is provided in the centre of one of the membranes 28, this membrane 28 being uppermost when the bag 20 is in use. As shown in FIG. 10, a degassing valve is formed by first cutting a hole 31 out of the centre of one of the membranes 28, over which the valve will be placed. A washer 29 made of uncured silicone rubber is positioned around the hole 31 on the outer face of the membrane 28. A hydrophobic PTFE membrane 30 with 0.2 µm pores and a thickness of 0.25 mm is laid over the washer 29, and a second washer 29 is placed on top. This is then repeated with a second PTFE membrane 30 and a third washer 29. When the bag 20 is to be assembled, the two silicone rubber membranes 28 are laid on top of one another. Two lengths of tubing for the inlet and outlet ports 23 are placed between the silicone rubber membranes 28, protruding slightly into what will be the interior of the assembled bag. The ports 23 are provided with valves 24. Next, room temperature vulcanising silicone rubber is applied to the untreated, smooth edges 27 of the silicone membranes 28, along which the membranes 28 are to be joined to form a bag configuration 20. Uncured silicone rubber is applied around the tubing where it lies adjacent to the smooth edges of the membranes 28. The constituents of the culture bag 20 so arranged are then welded or glued together using elevated temperatures and pressure. The edges of the silicone membranes 28 are sealed to form a bag 20, the degassing valve is formed from the layers of washers 29 and PTFE membrane 30, and the tubing for the ports 23 becomes integrated into the bag structure 20. In an alternative method, a gasket of uncured silicone rubber is placed between the membranes at their smooth edges. Upon the application of pressure and temperature, the gasket cures, fusing the edges of the membranes together to form the culture bag. The optional one or more additional cell attachment means may be appropriately positioned between the bag walls during the above described assembly method. Where the additional cell attachment means is a sheet, it may be welded to the bag walls along its edges, thereby creating compartments within the culture bag.

Figure 11:
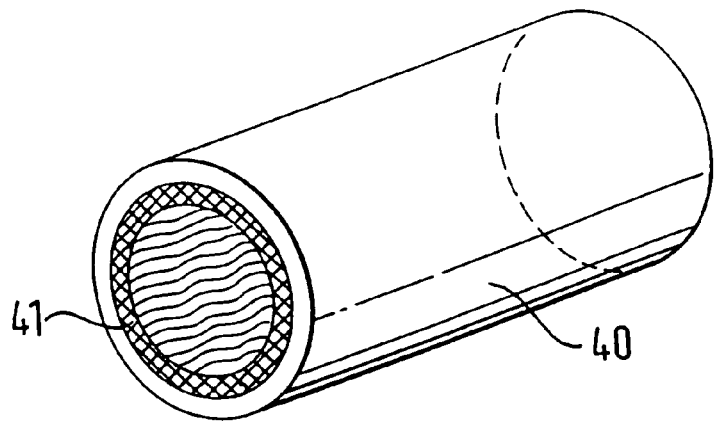
FIG. 11 is a diagrammatic illustration of a bio-reactor apparatus according to the third aspect of the invention.
Figure 12:
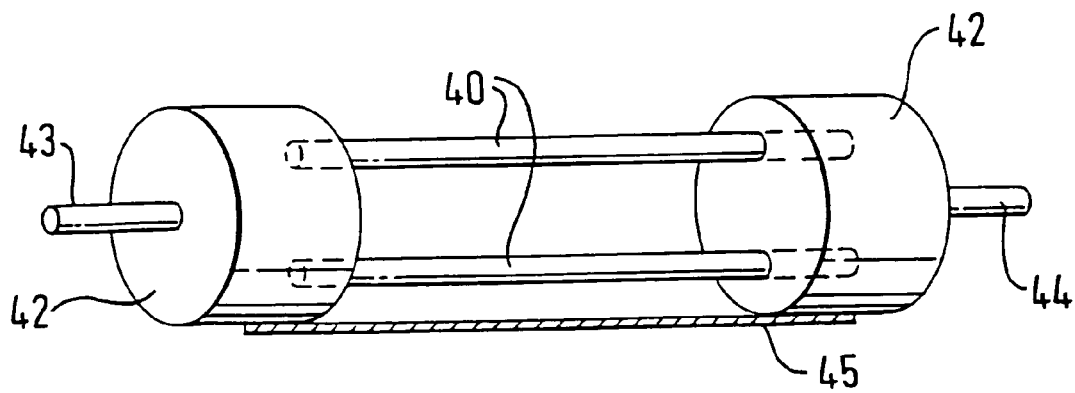
FIG. 12 is a silicone rubber tube from the bio-reactor of FIG. 11.
Figure 13:
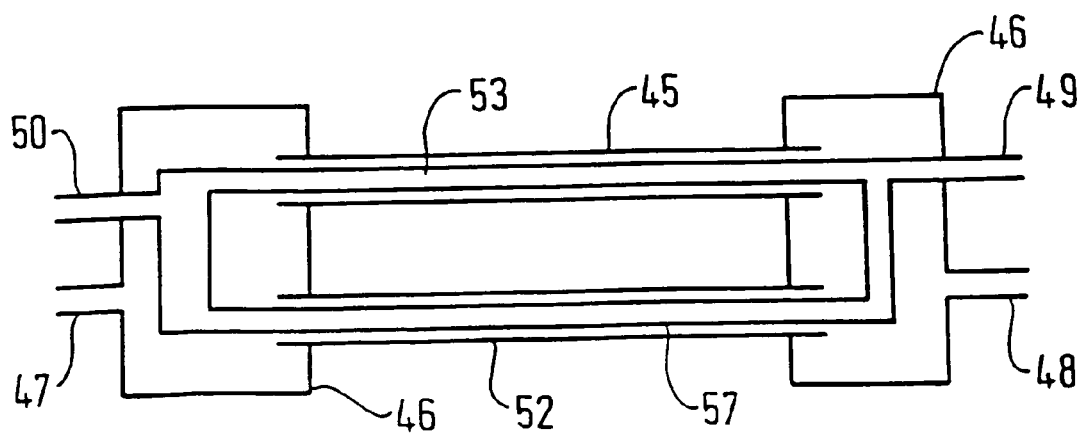
FIG. 13 is a cross-sectional side view of a bio-reactor apparatus with dialysis tubes.

In FIG. 11, a bio-reactor apparatus comprises two reactor tubes 40 (in practice, a larger number, such as seven or eight tubes, is generally preferred). Each reactor tube 40 carries internal and external coatings of textured silicone rubber 41. In use, in order to grow the cells on interior surfaces 41 of tubes 40, medium carrying cell lines is introduced through an inlet 43. Reactor tubes 40 are interconnected through distributors 42. One or more strengthening members 45 ensure rigidity of the assembly. The assembly is rotated on rollers (not shown), followed by evacuation of the liquid and subsequent passage of nutrient medium over the cells. The medium is introduced through the inlet 43 and issues from the outlet 44. The product is finally collected at the outlet 44. In FIG. 12, the reactor comprises a non-porous silicone rubber tube 40 carrying internal and external coatings of textured silicone rubber 41. In FIG. 13, dialysis tubes 51 are co-axially positioned within the reactor tubes 40. Cells are grown in the annular space 52 by the passage via introduction of medium comprising the cell line through the inlet 47. After removal of the liquid from the annular space through the outlet 48, the medium to be processed is passed through the dialysis tubes 51 via medium inlet 49, issuing at outlet 50. At the same time, the liquor to undergo the bio-reaction is passed through the reactor tubes via inlet 47, for collection at outlet 48.

Figure 14:
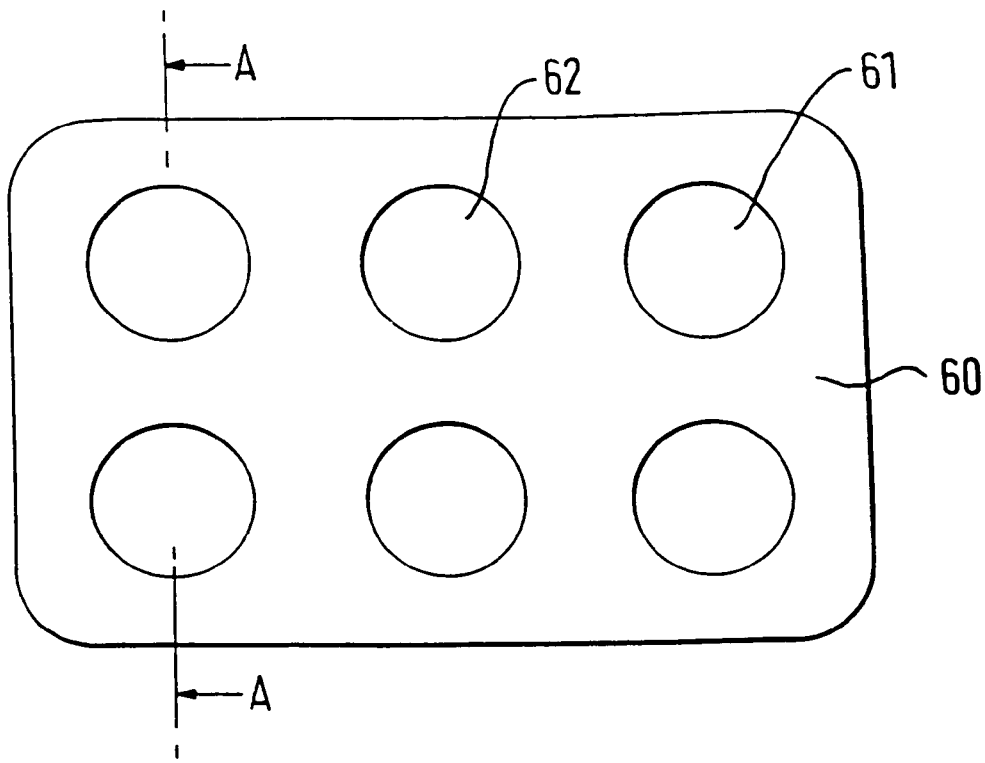
FIG. 14 shows plan view of a mictrotitre plate according to the fifth aspect of the invention.
Figure 15:
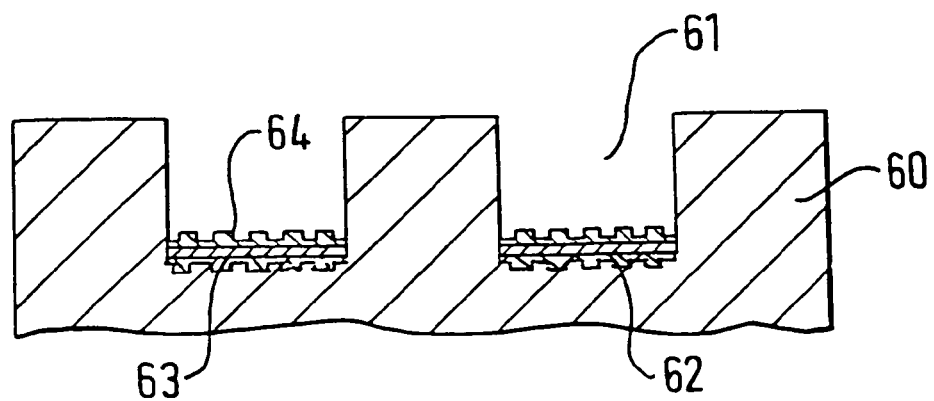
FIG. 15 shows a cross-sectional view of the plate of FIG. 14 along line A-A'.

In FIGS. 14 and 15, a standard microtitre plate 60 has wells 61 without base walls (either conventional microtitre plates are used and the base walls of the wells removed, or a microtitre plate is produced without any base walls). A non-porous silicone membrane 62 is attached to the bottom of the wells, the membrane comprises a silicone rubber sheet 63 having a textured surface 64 on both of its sides.

The invention claimed is:
1. A culture chamber comprising:
at least two gas-permeable membranes disposed substantially parallel to each other to form the culture chamber,
wherein each of the at least two membranes has a first end and a second end,
wherein each of the at least two membranes has a middle portion having an overlapping texture on an interior surface and an exterior surface;
an inlet port connected to the first end of each of the at least two membranes, the inlet port including a first valve member;
an outlet port connected to the second end of each of the at least two membranes, the outlet port including a second valve member,
wherein the first valve member and second valve member are capable of being opened and closed to allow medium to flow into and out of the culture chamber.
2. A culture chamber comprising:
at least two gas-permeable membranes disposed substantially parallel to each other to form the culture chamber,
wherein each of the at least two membranes has a first end and a second end, wherein each of the at least two permeable membranes has a middle portion having an overlapping texture on an interior surface and an exterior surface;
a semi-permeable membrane disposed in between the at least two permeable membranes, the semi-permeable membrane being substantially parallel to the at least two gas permeable membranes,
wherein the disposition of the at least two membranes and semi-permeable membrane form at least three compartments, an innermost compartment including an area inside the semi-permeable membrane and outermost compartments including areas in between the semi-permeable membrane and the at least two membranes;
an inlet port connected to the first end of each of the at least two permeable membranes, the inlet port including a first valve member;
an outlet port connected to the second end of each of the at least two permeable membranes, the outlet port including a second valve member,
wherein the inlet port and outlet port are provided in communication with the innermost compartment,
wherein the first valve member and second valve member are capable of being opened and closed to allow medium to flow into and out of the culture chamber.

3. A culture chamber comprising:
at least two gas-permeable membranes disposed across from each other to form the culture chamber,
wherein each of the at least two membranes has a non-textured first end, a non-textured second end and a middle portion having an overlapping texture on an interior surface and an exterior surface,
wherein the interior surface of each of the at least two membranes has a concave shape where a distance between the middle portion of the at least two membranes is greater than the distance between the first ends and second ends of the at least two membranes;
a degassing valve member disposed centrally in one of the at least two membranes;
an inlet port connected to the non-textured first end of each of the at least two membranes, the inlet port including a first valve member;
an outlet port connected to the second end of each of the at least two membranes, the outlet port including a second valve member,
wherein the first valve member and second valve member are capable of being opened and closed to allow medium to flow into and out of the culture chamber.

* * * * *